United States Patent
Krishnan et al.

(10) Patent No.: US 7,650,321 B2
(45) Date of Patent: Jan. 19, 2010

(54) TWO CLASSIFIER BASED SYSTEM FOR CLASSIFYING ANOMALOUS MEDICAL PATIENT RECORDS

(75) Inventors: Sriram Krishnan, Exton, PA (US); R. Bharat Rao, Berwyn, PA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 228 days.

(21) Appl. No.: 11/355,299

(22) Filed: Feb. 15, 2006

(65) Prior Publication Data

US 2006/0184475 A1    Aug. 17, 2006

Related U.S. Application Data

(60) Provisional application No. 60/653,290, filed on Feb. 16, 2005.

(51) Int. Cl.
*G06N 5/04* (2006.01)
*G06E 1/00* (2006.01)

(52) U.S. Cl. .............. 706/60; 706/20; 706/16
(58) Field of Classification Search .............. None
See application file for complete search history.

(56) References Cited

U.S. PATENT DOCUMENTS

| | | | |
|---|---|---|---|
| 6,760,715 B1 * | 7/2004 | Barnhill et al. | 706/16 |
| 6,789,069 B1 * | 9/2004 | Barnhill et al. | 706/12 |
| 6,882,990 B1 * | 4/2005 | Barnhill et al. | 706/16 |
| 2003/0105731 A1 | 6/2003 | Lapointe | |
| 2003/0120133 A1 | 6/2003 | Rao et al. | |
| 2003/0120134 A1 | 6/2003 | Rao et al. | |
| 2003/0120458 A1 | 6/2003 | Rao et al. | |
| 2003/0126101 A1 | 7/2003 | Rao et al. | |
| 2003/0130871 A1 | 7/2003 | Rao et al. | |
| 2005/0251013 A1 | 11/2005 | Krishnan et al. | |

OTHER PUBLICATIONS www.r2tech.com/main/home/index.php, downloaded Feb. 14, 2006.
www.r2tech.com/mammography/products/version 8 1.php, downloaded Feb. 14, 2006.
www.r2tech.com/mammography/products/version 8.php, downloaded Feb. 14, 2006.

* cited by examiner

*Primary Examiner*—David R Vincent
*Assistant Examiner*—Adrian L Kennedy

(57) ABSTRACT

Missing data is addressed in a medical decision support system. The classifier applied to the patient record with missing data is obtained as a function of the available data. For example, one of a plurality of different classifiers is selected based on the features available in the patient record to be classified. The different classifiers are developed using different feature sets. The classifier developed using a feature set closest to or a sub-set of the features available in the patient record is selected for classifying the patient record. As another example, features in a training set corresponding to features available in the patient record are used to build a classifier. The classifier is applied to the patient record by inputting the available features of the patient record.

10 Claims, 2 Drawing Sheets

TWO CLASSIFIER BASED SYSTEM FOR CLASSIFYING ANOMALOUS MEDICAL PATIENT RECORDS

RELATED APPLICATIONS

The present patent document claims the benefit of the filing date under 35 U.S.C. §119(e) of Provisional U.S. Patent Application Ser. No. 60/653,290, filed Feb. 16, 2005, the disclosure of which is hereby incorporated by reference.

BACKGROUND

The present embodiments relate to medical decision support systems. In particular, medical decision support systems operation is provided even with missing data. One problem in designing decision support classification is missing data. Some machine learning techniques do a better job in handling missing data than others.

In the case of clinical decision support for physicians, the issue of handling missing data has not been significant. Most machine learning algorithms have been based on interpretations of images. For example, classification is used in mammography computer assisted diagnosis (CAD) products to help identify potential lesions or calcifications. Since the only source of features is the image and the image is present, there is no issue of missing data. However, as decision support systems are extended to include heterogeneous sources of patient data, missing data may become an issue.

Not every patient will have all potential sources of information recorded in their patient record, either because a particular test was not done or results were not recorded. In an example of a decision support system to assist a physician in diagnosing breast cancer, the patient record may contain information about the woman, such as age and family history of cancer. In addition, the woman may or may not have screening mammograms from the past. Finally, some women may have undergone genetic tests, such as identification of the BRCA gene, to determine a propensity to breast cancer, but other may not have had the tests. Any one individual woman's patient record may only have a subset of information. Classifiers may not operate properly with missing inputs.

The missing values may be replaced with a substitute. In one approach, a global value replaces the missing data. The global value is an average, mean, median, or mode from a training set of data. Such a simple approach, however, could lead to incorrect conclusions.

In another approach, the most probable value replaces the missing data. The value may be estimated using inference, such as a Bayesian network. The value may be estimated from a distribution. Consider a set of features:

$$x = \{x_1 x_2 \ldots x_N\} \quad (1)$$

where $x_n$ is a feature, $n = 1 \ldots N$ and $N$ is the total number of possible features. Assuming only the first m features, $m < N$, are known for a particular patient, then one could estimate the joint probability as:

$$P(x_m, x_{m+1}, \ldots, x_N | x_1 \ldots x_N) \quad (2)$$

There are several approaches to solve this joint probability from a set of training data. However, as the number of features grows large, the ability to solve this problem becomes increasingly difficult. If a learning-based approach is used, then the amount of data to learn this conditional joint probability becomes extremely large. In the case of the breast cancer example, the number of pieces of information (i.e., features), such as the history information, physical examination, current and prior mammogram features, genomics data, and other information, can grow extremely large, such as being on the order of hundreds or even thousands of pieces of information. The creation of a joint probability may be difficult to construct.

BRIEF SUMMARY

By way of introduction, the preferred embodiments described below include methods, systems, and instructions for addressing missing data in a medical decision support system. The classifier applied to the patient record with missing data is obtained as a function of the available data. For example, one of a plurality of different classifiers is selected based on the features available in the patient record to be classified. The different classifiers are developed using different feature sets. The classifier developed using a feature set closest to or a sub-set of the features available in the patient record is selected for classifying the patient record. As another example, features in a training set corresponding to features available in the patient record are used to build a classifier. The classifier is applied to the patient record by inputting the available features of the patient record. Other than assigning a classifier based on the available features, one or more missing features may be replaced.

In a first aspect, a method is provided for addressing missing data in a medical decision support system. A set of M features in a patient record are identified. A processor assigns a classifier as a function of the M features. The patient record is classified with the classifier as a function of the M features.

In a second aspect, a computer readable storage media has stored therein data representing instructions executable by a programmed processor for addressing missing data in a medical decision support system. The instructions are for determining a list of features available from data for a current patient, obtaining a classifier as a function of the list, and applying the classifier to the data.

In a third aspect, a system is provided for addressing missing data in a medical decision support system. A memory is operable to store variables available for a patient record. A processor is operable determine a classifier as a function of the variables available for the patient record and operable to determine a diagnosis with the classifier and the variables.

In a fourth aspect, a computer readable storage media has stored therein data representing instructions executable by a programmed processor for addressing missing data in a medical decision support system. The instructions are for obtaining a patient record for medical decision support analysis, determining that information for at least one feature is missing from a patient record, selecting a classifier based on the missing information, and analyzing the patient record with the classifier.

In a fifth aspect, a computer readable storage media has stored therein data representing instructions executable by a programmed processor for addressing missing data in a medical decision support system. The instructions are for obtaining a patient record for medical decision support analysis, determining that information for at least one feature is missing from a patient record, training a classifier from a sub-set of training data, the sub-set free of information from the training data corresponding to the missing feature, and analyzing the patient record with the classifier.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

A set of L patient records is in a training set. Each of the L records may contain all N features from equation (1), resulting in:

$$y_p = \{y_{p1} y_{p2} \ldots y_{pN}\}, p=1 \ldots N \quad (3)$$

where y is a record or feature set having N features. For each of the records in the training set, a label or ground truth is recorded. For example, each record corresponds to breast cancer decision support, so each record is labeled as indicating or not indicating breast cancer.

Since not every patient may receive every test, this set of training records is usually collected in a very controlled setting, such as a clinical trial. A classifier is created based on this training set to label a new patient. However, the patient record for a new patient may only have m features, where m<N.

Rather than or in addition to substituting features into the new patient record, a classifier is obtained by considering only those m features. The m features are used to obtain the classifier, so that the classifier is associated with a training set based on the m features available for the new patient. Unfortunately, it is not known a-priori which m features will be available.

To assign the classifier as a function of the features available in a current patient record, the classifier is selected from a set of classifiers. A number of classifiers are constructed where each classifier is trained on a distinct set of features. In the case of a set of pre-computed filters (i.e., classifiers), classification may be performed quickly. The performance of each classifier may be validated beforehand, since it is known that one of a fixed number of classifiers will be used. Alternatively, the classifier is constructed "on-the-fly." Once the input features are available, the system constructs a classifier from the training data using only those features that exist in the current patient record. In the case of constructing classifiers during use of the system, the advantage is that new features for classification, and new cases to the training set, can be added with very little effort.

In the case of medicine, it is often difficult to get large, well-defined training sets with validated labels. Actual patient records are often times incomplete and inaccurate, making it difficult to use that data to build classification systems. A better classifier may be provided by using less than all the features or optimizing the training features to correspond to the features of a current patient record.

Figure 1:
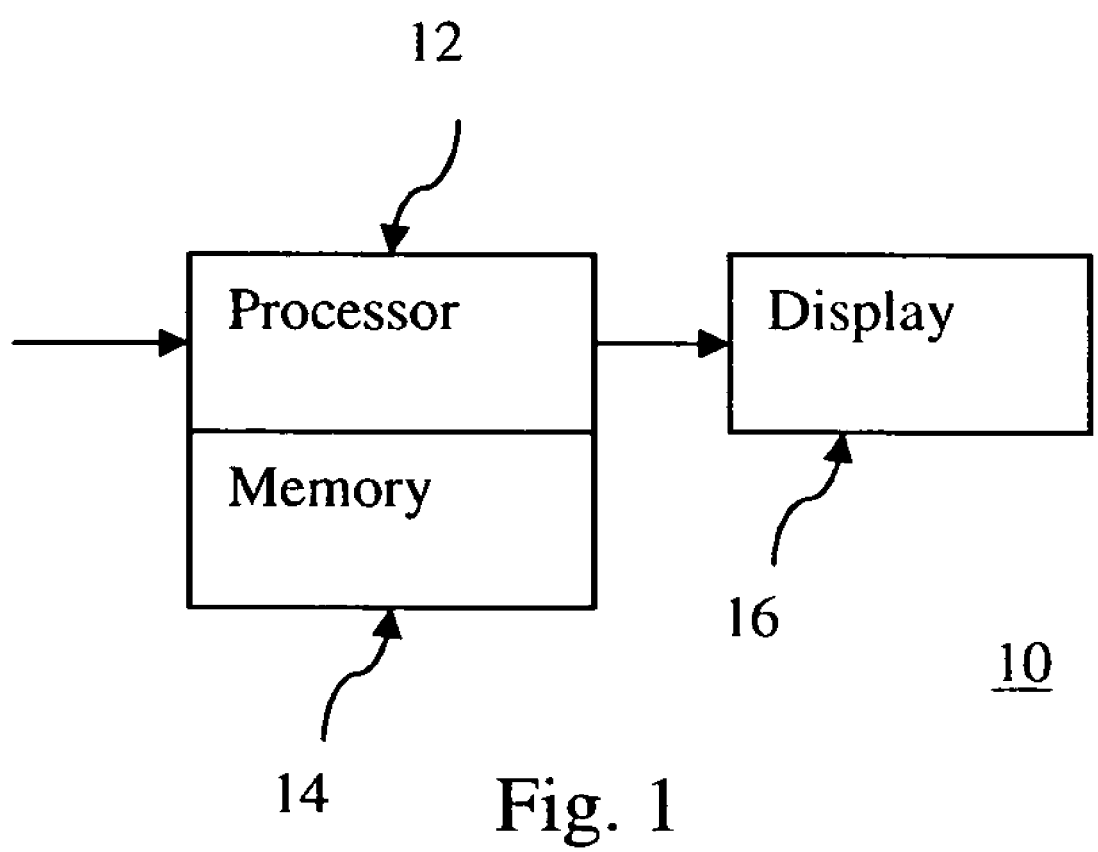
FIG. 1 is a block diagram of one embodiment of a system for addressing missing data in a medical decision support system.

FIG. 1 shows a system 10 for addressing missing data in a medical decision support system. The system 10 includes a processor 12, a memory 14 and a display 16. Additional, different or fewer components may be provided. The system 10 is a personal computer, workstation, medical diagnostic imaging system, network, or other now known or later developed system for providing decision support. For example, the system 10 is a computer aided diagnosis system. Automated assistance is provided to a physician for classifying a state appropriate for given medical information, such as the records of a patient. Assistance is provided for diagnosis of heart diseases, breast cancer, and/or lung cancer, but abnormality diagnosis may be performed for other medical abnormalities, such as associated with other organs. The automated assistance is provided after subscription to a third party service, purchase of the system 10, purchase of software or payment of a usage fee.

The processor 12 is a general processor, digital signal processor, application specific integrated circuit, field programmable gate array, analog circuit, digital circuit, combinations thereof or other now known or later developed processor. The processor 12 may be a single device or a combination of devices, such as associated with a network or distributed processing. Any of various processing strategies may be used, such as multi-processing, multi-tasking, parallel processing or the like. The processor 12 is responsive to instructions stored as part of software, hardware, integrated circuits, film-ware, micro-code or the like.

In one embodiment, the processor 12 determines a classifier as a function of variables available for a current or new patient record. The classifier may be determined in any now known or later developed way. For example, the processor 12 selects the classifier by matching the variables available for the current patient record to one of a plurality of classifiers. A bank of classifiers associated with distinct feature sets are pre computed and stored. The processor 12 determines the classifier with the feature set most closely matching the available features of the current patient record. Alternatively, the processor 12 determines the classifier trained with the feature set having all members within the available features. Where multiple classifiers qualify, the one with the most features is selected.

In another embodiment, the processor 12 determines the classifier by building the classifier from a sub-set of training data. The training data includes patient records each with variables for a plurality of features. A sub-set of the training data is selected. The sub-set includes training variables corresponding to the variables available for the current patient record, but not other variables. A classifier is then created from the sub-set of training data. The classifier is built with a limited number of features to classify based on the same features as available in the current patient record.

The classifier is constructed for each instance of a new patient record to be analyzed or only where another available classifier does not have a corresponding feature set. The classifier may be developed in minutes or hours. A customer or user of the system 10 uses the development of different classifiers rather than purchasing different classifiers based on an expected need.

The processor 12, whether a same device or a different device than used to determine the classifier, is operable to apply the classifier. The classifier is applied to the current patient record. The variables for the available features of the current patient record are input to the classifier. Applying the classifier determines a diagnosis. The classifier outputs a diagnosis, such as a conclusion, probability, location of concern or other information to assist with diagnosis.

The memory 14 is a computer readable storage media. Computer readable storage media include various types of volatile and non-volatile storage media, including but not limited to random access memory, read-only memory, programmable read-only memory, electrically programmable read-only memory, electrically erasable read-only memory, flash memory, magnetic tape or disk, optical media and the like. The memory 14 may be a single device or a combination of devices. The memory 14 may be adjacent to, part of, networked with and/or remote from the processor 12.

The memory 14 stores a patient record. The patient record is input manually by the user and/or determined automatically. The patient record may be formatted or unformatted. The patient record resides in or is extracted from different sources or a single source. The patient record includes variables available for a current patient record. The variables correspond to features, such as medical history, pain indication, lump indication, age, genetic information, test results, family history or other sources of information. The patient record may include one or more images of a same or different type. The processor 12, a different processor or the user may extract variables from the image. The variables correspond to features of the image. Any now known or later developed patient record format, features and/or technique to extract features may be used.

In one embodiment, the memory 14 stores a plurality of classifiers. Each classifier may be stored as a matrix, but more complex classifier algorithms, instruction sets, logic, or tools may alternatively or additionally be stored.

Each of the classifiers is a different or same type of classifier. Any now known or later developed classifiers may be used, such as support-vector machine (SVM), decision tree, neural net, Bayesian classifier, or combinations thereof. The classifiers corresponds to different sets of variables. The classifiers are optimized or designed for classifying with different input features.

A classifier is provided for each possible combination of input features. For example, one hundred different features are possible. Ten thousand different classifiers are provided. Alternatively, a fewer number of classifiers is provided. For example, one or more features may be required for classification, so all the classifiers include those required features. In another example, classifiers for a sub-set of all possible feature combinations are provided. The processor 12 may select the classifier using most of the available features for the current patient record and none of the features not available in the current patient record. Alternatively, the processor 12 may select the classifier with the most similar feature set. Any features missing from the current patient record are substituted based on probability, average, another statistic, distribution or inference.

In another embodiment, the memory 12 stores training data. The training data is a collection of two or more previously acquired patient records and corresponding labels or ground truths. For example, hundreds, thousands or tens of thousands of patient records are obtained and stored. In one embodiment, the records are originally created as part of a clinical study. In other embodiments, the records are gathered independent of a clinical study, such as being collected from one or more hospitals.

Each training set patient record includes extracted variables for a plurality of features. The different patient records have the same extracted features, but one or more patient records may have fewer or a greater number of features. Alternatively, one or more of the patient records includes information to be used for extracting features, such as including an image. Any format may be used for maintaining and storing the training data.

In another embodiment, the memory 12 stores training data and a bank of classifiers. The system 10 is operable to implement determining the classifier by either selection from a bank or constructing the classifier as a function of a feature set. Alternatively, the system 10 implements both approaches for a same current patient record to be analyzed.

The display 16 is a CRT, monitor, flat panel, LCD, projector, printer or other now known or later developed display device for outputting determined information. For example, the processor 12 causes the display 16 at a local or remote location to output data indicating a possible diagnosis, a probability associated with one or more possible diagnoses, an image with marked locations of interest, or other medical decision assistance associated with the current patient record. The output may be stored with or separate from the patient record.

The memory 14 stores instructions for the processor 12. In one embodiment, the instructions are stored on a removable media drive for reading by a medical diagnostic imaging system or a workstation. An imaging system or workstation uploads the instructions. In another embodiment, the instructions are stored in a remote location for transfer through a computer network or over telephone lines to the imaging system or workstation. In yet other embodiments, the instructions are stored within the imaging or assistance system on a hard drive, random access memory, cache memory, buffer, removable media or other device.

The processor 12 is programmed with and executes the instructions. The instructions are for addressing missing data in a medical decision support system. The functions, acts, methods or tasks illustrated in the figures or described herein are performed by the programmed processor 12 executing the instructions stored in the memory 14. The functions, acts, methods or tasks are independent of the particular type of instructions set, storage media, processor or processing strategy and may be performed by software, hardware, integrated circuits, film-ware, micro-code and the like, operating alone or in combination.

In one embodiment, the instructions are for obtaining a patient record for medical decision support analysis. Medical data, such as the patient record or portions of the patient record, is input to the processor 12 or the memory 14. The medical data is from one or more sources of patient information. For example, one or more medical images are input from ultrasound, MRI, nuclear medicine, x-ray, computer thermography, angiography, and/or other now known or later developed imaging modality. Additionally or alternatively, non-image medical data is input, such as clinical data collected over the course of a patient's treatment, patient history, family history, demographic information, billing code information, symptoms, age, genetics or other indicators of likelihood related to the abnormality or disease detection being performed. For example, whether a patient is female, has a history of breast cancer problems, has a detectable lump, has pain, has a family history of breast cancer or is old may indicate a likelihood of breast cancer. Other features may be used for breast cancer determination. The same and/or different features may be used for assisted diagnosis of other diseases.

The information is input by a user. For example, the instructions control a user interface to solicit entry of information manually by an operator. Alternatively, the information is extracted automatically, such as described in U.S.

Publication Nos. 2003/0120458, 2003/0120133, 2003/0120134, 2003/0126101 or 2003/0130871, which are incorporated herein by reference. Information is automatically extracted from patient data records, such as both structured and un-structured records. Probability analysis may be performed as part of the extraction for verifying or eliminating any inconsistencies or errors. The system may automatically extract the information to provide some missing data. The processor 12 performs the extraction of information. Alternatively, other processors perform the extraction and input results, conclusions, probabilities or other data to the processors 12. Other automated extraction or importing of a patient record may be used, such as instructions for a routine to import patient record information from a structured database.

Instructions cause the processor 12 to determine a list of features available from data for the current patient. For example, the instructions call for identifying variables for a particular set of N features. The processor 12 determines which of the N features have variables. Alternatively or additionally, the processor 12 determines that information for at least one feature is missing from a patient record. In other embodiments, the processor 12 maintains a record of extracted features as a list of available features for the current patient record. A list of structured data cells with variables may be formed.

Instructions cause the processor 12 to obtain a classifier as a function of the list of available features. More than one classifier may be obtained. In one embodiment, the classifier is selected from a plurality of prior developed or previously trained classifiers. The prior developed classifiers are operable with different lists of features. More than one classifier may be provided in the bank of classifiers for operating with a given list of features. One or more classifiers are selected based on the missing information or list. The classifier with the best feature match to the list of features of the current patient record is selected. The classifier may operate with fewer features than available in the current patient record.

In another embodiment, the processor 12 obtains the classifier by constructing the classifier from training data. Values for the features or a sub-set of features in the list for the current patient record are extracted from the previously collected training data. This sub-set of the training data is free of information corresponding to any missing features of the current patient record. Alternatively, one or more missing features in the current patient record are obtained in the training set and used to calculate or as substitute values. The processor 12 trains a classifier from the selected sub-set of the training data. The classifier is trained to operate with the available features of the current patient record with or without some substitute information. Other processes for selecting the sub-set and training the classifier may be used.

The obtained classifier may be optimized. Using manual input or user feedback, the classifier is tuned. Alternatively, automatic optimization is performed.

The instructions cause the processor 12 to apply the obtained classifier to the current patient record. The variables for the available features are input into the classifier. The current patient record is analyzed with the classifier. The classifier outputs information for the current patient record.

Instructions may be provided for determining and outputting an estimate of performance of the classifier. For example, the processor 12 calculates a ROC curve, specificity, sensitivity or other parameter. The training data is used to determine the performance, such as using a leave one out approach. As another example, a previously calculated performance for the selected classifier from the bank of classifiers is acquired. The estimate of performance is output with the output of the classifier or prior to any classifying of the current patient record. The estimate of performance may highlight areas of concern or reassure the operator or medical professional.

The set of features may be increased to include features not available but reliably substituted in the current patient record. The set of features may be decreased or otherwise reorganized into a sub-set of the available features.

The instructions cause the processor 12 to repeat obtaining, determining, selecting and analyzing for a different patient record. To assist in diagnosis of a new patient, the same system 10 is used. Available features are determined and a classifier is obtained based on the available features of the new patient record. The same system 10 operates with different patient records, resulting in different classifiers being used. A "one classifier fits all" approach may be avoided, providing versatility on a patient-by-patient basis. The same training data may be used by the system 10 to create different classifiers as appropriate for the different patient records. The training data may also be updated, such as a structured update or by accumulating some or all of the new patient records as part of the training data once an actual diagnosis or label is known.

Figure 2:
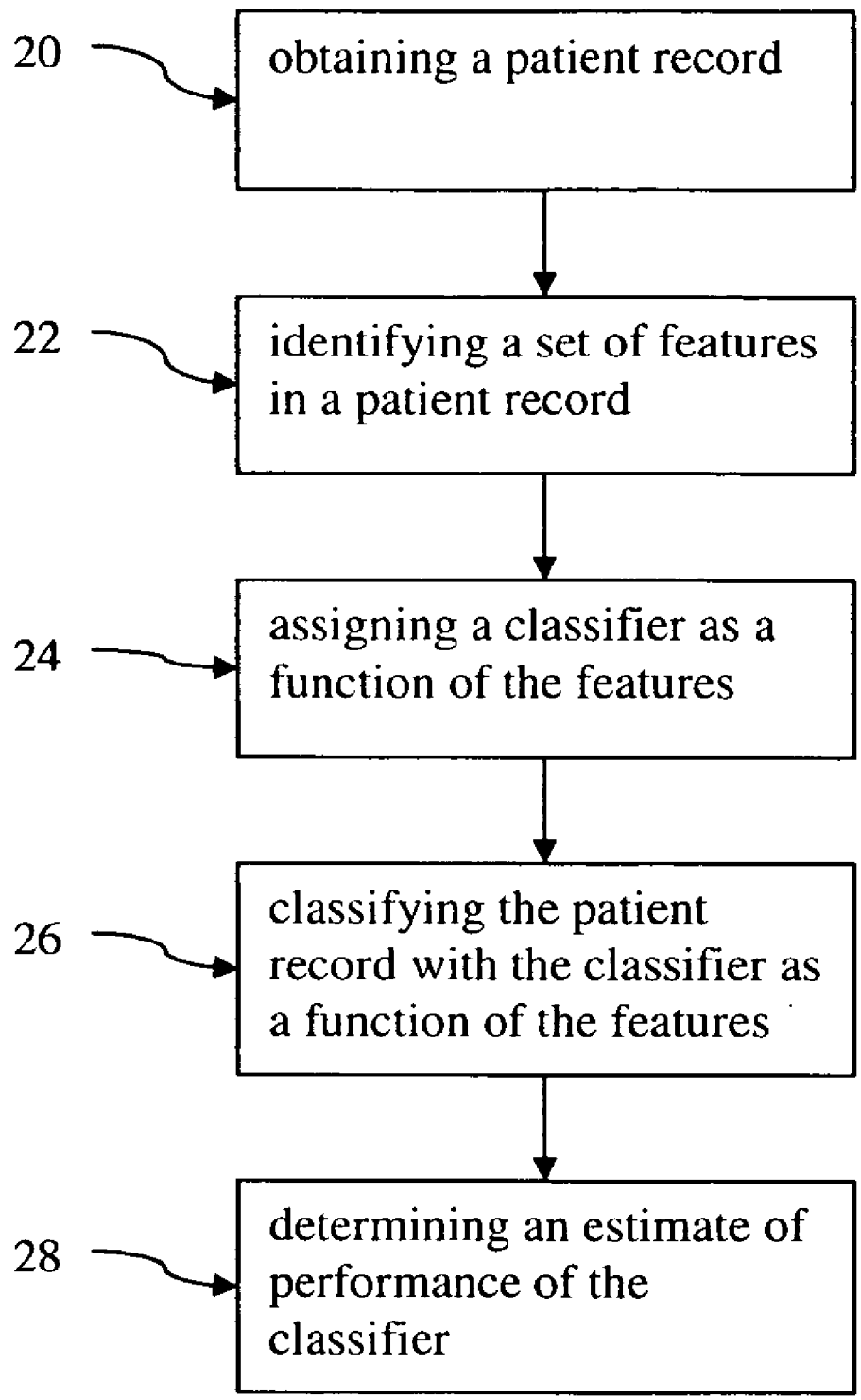
FIG. 2 is a flow chart diagram showing one embodiment of a method for addressing missing data in a medical decision support system.

FIG. 2 shows a method for addressing missing data in a medical decision support system. The method is implemented using the system 10 of FIG. 1 or a different system. Additional, different or fewer acts than shown in FIG. 2 may be provided. For example, act 28 may not be performed. The acts are performed in the order shown or a different order. The acts may be performed automatically, manually, or combinations thereof. For example, acts 20 and 22 are performed manually and/or automatically, and acts 24 and 26 are applied automatically by a processor.

In act 20, data for a new patient record is obtained. For example, the medical data is obtained automatically, through user input or a combination thereof for a particular patient being examined. The medical data is structured or unstructed.

In act 22, a set of M features are identified in the patient record. Features are extracted from the patient record. Where some information is not available, some features may not be extracted. For structured patient records, the features having a value or information are extracted. Each of the features available from the current patient record is identified. In alternative or additional embodiments, the patient record is reviewed to determine any missing features from a set of possible features. A knowledge base of possible features, such as features available in all or most of the patient records in a training set or features indicated as making a diagnosis more or less probable based on studies or medical knowledge, is compared against the current patient record. A sub-set of the possible features corresponding to features available in the current patient record is identified, identifying the missing features.

In act 24, a processor assigns a classifier as a function of the available features for the current record. Any now known or later developed process for assigning may be used.

In one embodiment, the processor assigns the classifier by selecting from a collection of at least two classifiers. Any number of classifiers may be provided, such as fewer than, an equal number or more than the number of available features. For example, classifiers are provided for the most common combinations of features in patient records for the type of diagnosis.

A bank of classifiers is constructed prior to use. The number of classifiers in one embodiment is:

$$\sum_{m=1}^{N} \binom{N}{m}$$

where N is the number of possible features and m is the number of available features in a current patient record. The appropriate classifier is chosen based on which features are available in the current patient record. For large values of N, this could lead to a very large set of classifiers. However, in most instantiations of a classifier, the memory requirements of each actual classifier are small, allowing many classifiers to be stored.

The classifiers are operable with different sets of features. The classifiers are trained, designed or optimized to receive particular features as inputs. Different classifiers may correspond to different feature sets. One or more classifiers operable with the features available for the current patient record are selected. The operable classifiers include classifiers for the same features as the current patient record or a sub-set of the available features of the current patient record. Classifiers using input features not available in the current patient record are not selected. Alternatively, one or more selected classifiers may have inputs missing in the current patient record, but the missing information may be substituted with other information.

In another embodiment of act 24, the processor assigns the classifier by constructing the classifier. The processor selects features from training set patient records. The training set patient records do not include the current patient record. Automated feature selection may be based on machine-learnt processes for feature selection and/or programmed identification. Alternatively, manual input assists in selection of features. The selected features are the set or a sub-set of the features available for the current patient record. Rather than using all of the features of the training set patient records, features are selected based on the features available in the patient record to be classified. Unselected features are not used for training the classifier, but may be used.

The training set may contain incomplete information. Where one or more patient records of the training set do not include a feature available in the current patient record, these training set patient records are not used or are unselected. The classifier is built to use only those cases in the training set which have all of the features contained in the test patient. Alternatively, the training set is updated or cleaned-up by filling in the missing data using actual data or substitute values. Alternatively, a classifier is built for operation with fewer than all of the available features of the current patient record.

After selecting the training set patient record information, the processor constructs a classifier from the selected set of features from the training set patient records. The classifier is built with a single pass, or an iterative process is provided. Different combinations of some or all of the available features from the selected set are tried. Different types of classifiers or combinations of classifiers may be attempted. All possible combinations are attempted and the best performing one or ones are assigned. Alternatively, a first sufficiently performing classifier is assigned and no further classifiers are built. In other embodiments, the different combinations or iterations are guided logically or based on a knowledge base. Any possible tuning may be provided, such as automated tuning and/or manual tuning based on information in the training data. The classifier may be applied to the training data for tuning.

Construction of the classifier is performed separately for different patient records to be analyzed. Alternatively, the construction is performed separately for each current patient record with different or sufficiently different available features sets. The classifier or classifiers are built to classify based on the available or a sub-set of the available features of the current patient record.

The assignment occurs as needed without requiring a user to generalize one classifier for all patient records to be analyzed. The user may not need to purchase a different classifier since the needed classifier is built or selected based on the patient record to be analyzed. Additional classifier options or training data information may be purchased to alter the operation of the assignment of the classifier or to provide more options.

Any type of classifier may be assigned. Depending on the available features, a single type of classifier may be available for selection or building. Alternatively, different types are available. The classifier is assigned from a support-vector machine (SVM), decision tree, neural net, Bayesian classifier, combinations thereof (e.g., hierarchal classification) or other now known or later developed classifier. Different classifiers may be used for different feature sets or in different iterative constructions since any specific problem may be more amenable to one classification approach over another.

In act 26, the assigned classifier classifies the patient record as a function of all or some of the available features of the current patient record. A processor automatically classifies between a normal state and one or more disease states. Probabilities may be determined. The disease states represent all possible disease states but may alternatively represent fewer than all possible disease states. The classification may be between a group of two or more states and another group of two or more states. The classification is performed with neural network, filter, algorithm, or other now-known or later developed classifier or classification technique. The classifier is configured or trained for distinguishing between the desired states.

In act 28, the processor determines an estimate of performance of the classifier. The system may provide the sensitivity, specificity, an ROC curve, or some other estimate of the performance of the classifier to the user. For example, the estimate is determined by a table of performance estimates of the selectable classifiers. As another example, the estimate is determined by applying the constructed classifier to the training data. A leave-one-out or another approach provides an indication of the performance of the classifier. Alternatively, statistical performance for the system based on application of multiple classifiers is published.

The estimate is output, such as for the system or with each associated analysis of a current patient record. The estimate of performance may provide feedback as to whether the data collected from the patient is sufficient to label the patient with the system or automatically.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method for addressing missing data in a medical decision support system, the method comprising:
   identifying a set of M features in a patient record;
   assigning, with a processor, a classifier as a function of the M features; and
   classifying the patient record with the classifier as a function of the M features;
   wherein assigning comprises selecting, with the processor, from a collection of at least two classifiers, each of the at least two classifiers operable with different sets of features;
   wherein selecting, with the processor, comprises selecting the classifier for the set of M features or a sub-set of the M features and not selecting any classifier with at least one feature not in the set of M features.

2. The method of claim 1 wherein identifying comprises identifying each of the M features.

3. The method of claim 1 wherein identifying comprises determining missing features from a set of N possible features, the set of M features being a sub-set of the set of N possible features.

4. The method of claim 1 wherein assigning comprises assigning from different types of classifiers.

5. The method of claim 1 further comprising:
   determining, with the processor, an estimate of performance of the classifier; and outputting the estimate.

6. In a computer readable storage media having stored therein data representing instructions executable by a programmed processor for addressing missing data in a medical decision support system the storage media comprising instructions for:
   identifying a set of M features in a patient record;
   assigning with a processor a classifier as a function of the M features; and
   classifying the patient record with the classifier as a function of the M features;
   wherein assigning comprises selecting, with the processor, from a collection of at least two classifiers, each of the at least two classifiers operable with different sets of features;
   wherein selecting, with the processor, comprises selecting the classifier for the set of M features or a sub-set of the M features and not selecting any classifier with at least one feature not in the set of M features.

7. The computer readable media of claim 6 wherein identifying comprises identifying each of the M features.

8. The computer readable media of claim 6 wherein identifying comprises determining missing features from a set of N possible features, the set of M features being a sub-set of the set of N possible features.

9. A system for addressing missing data in a medical decision support, the system comprising:
   a memory operable to store features available for a patient record and a collection of at least two classifiers; and
   a processor operable to identify a set of M of the features in the patient record, to assign a classifier as a function of the M features, and classify the patient record with the classifier as a function of the M features, wherein the processor is operable to assign by selecting from the collection of at least two classifiers, each of the at least two classifiers operable with different sets of features, and wherein selecting comprises selecting the classifier for the set of M features or a sub-set of the M features and not selecting any classifier with at least one feature not in the set of M features.

10. The system of claim 9 wherein the processor is operable to identify by determining missing features from a set of N possible features the set of M features being a sub-set of the set of N possible features.

* * * * *